United States Patent
Wiesner et al.

(10) Patent No.: US 11,491,296 B2
(45) Date of Patent: Nov. 8, 2022

(54) AUTONOMOUS AIRCRAFT AND METHOD FOR PROVIDING VENTILATION TO PEOPLE

(71) Applicant: VOLKSWAGEN AKTIENGESELLSCHAFT, Wolfsburg (DE)

(72) Inventors: Thomas David Wiesner, Braunschweig (DE); Mathis Borchers, Nienburg (DE); Frank Minter, Lehre OT Beienrode (DE); Katrin Riedel, Vordorf Rethen (DE)

(73) Assignee: Volkswagen Aktiengesellschaft

( * ) Notice: Subject to any disclaimer, the term of this patent is extended or adjusted under 35 U.S.C. 154(b) by 344 days.

(21) Appl. No.: 16/835,791

(22) Filed: Mar. 31, 2020

(65) Prior Publication Data
US 2020/0316331 A1 Oct. 8, 2020

(30) Foreign Application Priority Data

Apr. 2, 2019 (DE) ...................... 10 2019 204 676.2

(51) Int. Cl.
*A61M 16/10* (2006.01)
*A61M 16/06* (2006.01)
(Continued)

(52) U.S. Cl.
CPC ........ *A61M 16/1005* (2014.02); *A61M 16/06* (2013.01); *B64C 39/024* (2013.01);
(Continued)

(58) Field of Classification Search
CPC . B64C 39/02; B64C 39/024; B64C 2201/128; B64C 2201/126;
(Continued)

(56) References Cited

U.S. PATENT DOCUMENTS

| 8,930,044 | B1* | 1/2015 | Peeters | ................ G08G 5/0069 |
| | | | | 709/201 |
| 8,948,935 | B1* | 2/2015 | Peeters | .................. G05D 1/102 |
| | | | | 709/201 |

(Continued)

FOREIGN PATENT DOCUMENTS

| CN | 107117298 A | 9/2017 |
| CN | 108706098 A | 10/2018 |
| DE | 102009015928 A1 | 11/2009 |
| JP | 2018134903 A | 8/2018 |
| WO | 2015076886 A2 | 5/2015 |
| WO | 2017147188 A1 | 8/2017 |

OTHER PUBLICATIONS

Ingenieur; Drone Rushes to Aid in Cardiac Arrest with Defibrallator; Dec. 12, 2019; downloaded from https://www.ingenieur.de/technik/fachbereiche/medizin/drohne-eil-herzstillstand-defibrillator-hilfe/.

*Primary Examiner* — Benjamin P Lee
(74) *Attorney, Agent, or Firm* — Barnes & Thornburg, LLP

(57) ABSTRACT

An autonomous aerial vehicle for ventilating persons. The ventilation becomes necessary as a result of fires, accidents, or medical emergencies. In these and comparable cases, the aerial vehicle aids for ventilating a person quickly and independently of the transport links of a location or the traffic situation at the time so the state of the person is stabilized until the arrival of an emergency doctor or other rescue workers and the chances of survival improves. The aerial vehicle provides positional determination inside and/or outside buildings, recording of the surrounding area, ventilation of at least one person, and a communication method or mechanism.

12 Claims, 1 Drawing Sheet

(51) Int. Cl.
*B64C 39/02* (2006.01)
*B64D 25/00* (2006.01)
*B64D 45/00* (2006.01)
*B64D 47/02* (2006.01)
*B64D 47/08* (2006.01)

(52) U.S. Cl.
CPC .......... *B64D 25/00* (2013.01); *B64D 45/00* (2013.01); *B64D 47/02* (2013.01); *B64D 47/08* (2013.01); *A61M 2202/0208* (2013.01); *A61M 2205/3576* (2013.01); *A61M 2205/581* (2013.01); *A61M 2205/583* (2013.01); *B64C 2201/027* (2013.01); *B64C 2201/12* (2013.01); *B64D 2231/025* (2013.01)

(58) Field of Classification Search
CPC ........ B64C 2201/141; B64C 2201/027; A61N 1/3904; A61N 1/39; G16H 40/67; B64D 1/08
See application file for complete search history.

(56) References Cited

U.S. PATENT DOCUMENTS

| | | | |
|---|---|---|---|
| 8,983,682 B1* | 3/2015 | Peeters | G16H 40/20 |
| | | | 701/2 |
| 9,051,043 B1* | 6/2015 | Peeters | H04L 67/12 |
| 9,773,419 B1* | 9/2017 | Gordon | G08G 5/0078 |
| 9,849,979 B2* | 12/2017 | Peeters | B64C 39/024 |
| 9,994,315 B2* | 6/2018 | Walker | A61B 5/0205 |
| 10,259,578 B2* | 4/2019 | Sekine | B64C 39/02 |
| 10,467,885 B2* | 11/2019 | Trundle | H04B 7/18504 |
| 2015/0148988 A1* | 5/2015 | Fleck | B64D 1/14 |
| | | | 701/2 |
| 2015/0166176 A1 | 6/2015 | Hester, Jr. et al. | |
| 2017/0137124 A1* | 5/2017 | Walker | A61B 5/08 |
| 2017/0341745 A1* | 11/2017 | Sekine | B64C 39/02 |
| 2018/0147429 A1* | 5/2018 | Won | B64C 25/405 |
| 2018/0237276 A1 | 8/2018 | Bialkowski et al. | |
| 2018/0297702 A1* | 10/2018 | Walker | G08B 25/08 |
| 2018/0307223 A1 | 10/2018 | Peeters et al. | |
| 2021/0299311 A1* | 9/2021 | Yu | B64C 39/02 |

* cited by examiner

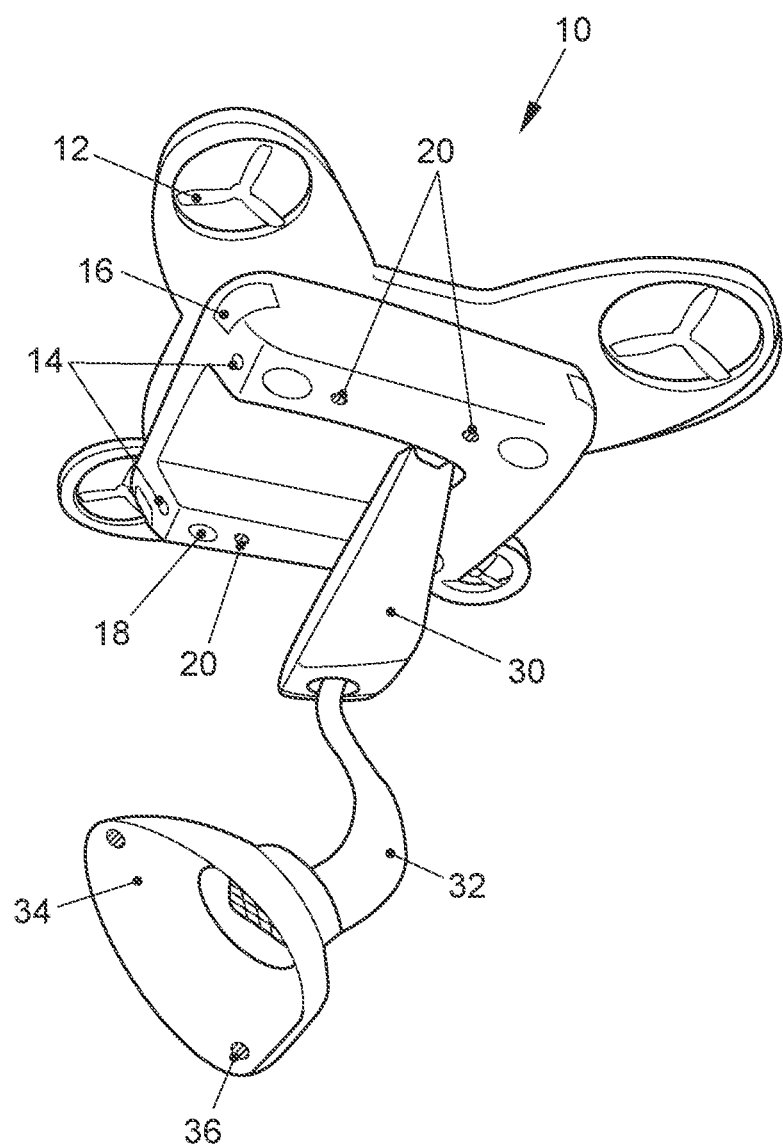

AUTONOMOUS AIRCRAFT AND METHOD FOR PROVIDING VENTILATION TO PEOPLE

PRIORITY CLAIM

This patent application claims priority to German Patent Application No. 10 2019 204 676.2, filed 2 Apr. 2019, the disclosure of which is incorporated herein by reference in its entirety.

SUMMARY

Illustrative embodiments relate to an autonomous aerial vehicle for ventilating persons and to a method for ventilating persons with the disclosed aerial vehicle.

BRIEF DESCRIPTION OF THE DRAWINGS

Disclosed embodiments are explained below with reference to the drawing, in which:

FIG. 1 shows a perspective view of an exemplary aerial vehicle in a configuration given, by way of example, obliquely from below.

DETAILED DESCRIPTION

In the event of accidents or in the case of a disaster, the time within which rescue workers reach the scene to help the injured is decisive for whether they survive or to what extent they suffer consequential effects. In cases in which a person is no longer breathing, or breathing is made more difficult or impossible, such as in the case of fires, accidents on or in water involving the risk of drowning and the like, the time to the arrival of rescue workers is critical. In Germany, there is an official response time, that is to say a time period within which rescue workers and/or fire services are supposed to reach those injured or affected in 95% of cases occurring. This response time is specific to each federal state and is generally between 10 and 15 minutes. However, in cases where breathing is restricted or has stopped, this time period may already be too long to prevent the person injured or affected from suffering consequential effects or dying.

The time that a team of medical personnel, that is to say emergency doctors and/or paramedics, needs to arrive at the location concerned depends among other factors on the distance and the traffic at the time of the accident. Although rescue workers and fire services can use flashing lights and sirens to assist their progress, and thereby advance more quickly, there may always be situations in which advancement is hindered. The time within which a rescue team arrives is also influenced by access itself, for example, if in the event of a disaster roads are no longer passable. It is therefore necessary to develop solutions for how help can be provided quickly in cases in which ventilation is necessary, optionally until the arrival of an emergency doctor and/or paramedic and irrespective of traffic or transport links to the location concerned.

Various aerial vehicles for rescuing injured persons are known from the prior art. However, they are often manned, restricted to outdoor use, that is to say situations outside buildings, and/or are equipped for medical first aid in general.

www.ingenieur.de/technik/fachbereiche/medizin/drohne-eil-herzstillstand-defibrillator-hilfe/discloses a drone which can autonomously transport medical equipment for first aid to a person in need of help. This drone is also suitable for delivering breathing equipment to people threatened by fire.

DE 10 2009 015 928 A1 discloses a ventilating device for providing ventilation while allowing for an optional addition of oxygen. Methods or mechanisms are provided by which breathing gas can be enriched with oxygen and supplied to the patient by way of a corresponding mask.

Disclosed embodiments provide an aid by which, in the emergencies mentioned, ventilation can be provided quickly, independently of the location of the emergency and the traffic situation at the time, to ventilate a person affected by a medical emergency until the arrival of an emergency doctor and/or paramedic and to increase the chances of survival.

This is achieved by an exemplary autonomous aerial vehicle and the disclosed method.

An exemplary autonomous aerial vehicle is designed to ventilate at least one person. It is therefore designed with methods or mechanisms for positional determination inside and/or outside buildings, methods or mechanisms for recording the surrounding area, methods or mechanisms for ventilating the at least one person, and communication methods or mechanisms for exchanging positional data and/or information.

The aerial vehicle is designed with methods or mechanisms for facial detection. On the basis of the facial detection, initially persons can be detected as such. Among other things, this also makes it possible to search for and find a person when only an approximate locality of the person is known. For example, the facial detection may be realized in a way known per se on the basis of images or videos that are provided by the methods or mechanisms for recording the surrounding area and suitable mechanisms for evaluating the images. The facial detection also makes it possible to detect the mouth and nose of persons to be ventilated, so that the disclosed aerial vehicle can place an oxygen mask specifically and correctly onto the face of the person to be ventilated.

An autonomous aerial vehicle should be understood as meaning that this aerial vehicle reaches the location concerned without a pilot. On the basis of information with respect to the position of a rescue situation, the aerial vehicle flies to the location concerned to provide the ventilation. In the context of the disclosure, a rescue situation is understood as meaning an emergency in which at least one person has to be ventilated. Among the situations where the necessity for ventilation may arise are fires, cases of disaster and/or when rescuing people from drowning. Ventilation may also be necessary in accidents of other kinds.

The disclosed autonomous aerial vehicle is therefore designed with methods or mechanisms for positional determination inside and/or outside buildings.

Positional determination by GPS may be mentioned by way of example as a customary method or mechanism for determining the position of an object outside buildings, but the configuration of the disclosed autonomous aerial vehicle is not to be restricted to this. Other methods or mechanisms that allow the exact position of the autonomous aerial vehicle inside and/or outside buildings to be determined are also covered by the disclosure and are further explained below. In this respect, various methods for the positional determination of the autonomous aerial vehicle, which allow positional determination either in the interior of buildings or outside buildings or both inside and outside buildings, can be used.

The position of the autonomous aerial vehicle is in this case not only relevant to it progressing and finding its way, but also to a rescue system at a higher level, such as, for example, a rescue control center which coordinates and controls rescue operations. It must therefore also be possible for the position to be transmitted from the autonomous aerial vehicle to others, for example, a control center for rescue operations. This also serves for finding persons to be ventilated more quickly when an emergency doctor and/or paramedic arrives at the location concerned. On the basis of the position of the autonomous aerial vehicle, the person to be ventilated can be found quickly.

Furthermore, the autonomous aerial vehicle comprises methods or mechanisms for recording the surrounding area. On arrival of the aerial vehicle at the location concerned, the overall situation at the time must first be recorded and assessed. Even if information on the location concerned and the rescue situation were previously transmitted and evaluated during an emergency call, the conditions at the location concerned may change quickly and sometimes also unexpectedly. Therefore, it is beneficial if the autonomous aerial vehicle provides methods or mechanisms for recording the surrounding area. In this way, the autonomous aerial vehicle is intended to record the surrounding area in a spatial sense, that is to say whether and which obstacles or dangers hamper the rescue situation, the number of persons to be ventilated and/or deviations from the previously transmitted information with respect to the rescue situation. This may take place both in an automated manner within the autonomous aerial vehicle, but also by the transmission of the recorded surrounding area to a rescue control center.

The autonomous aerial vehicle is designed with methods or mechanisms for ventilating the at least one person. This should be understood as meaning all methods, mechanisms, devices and equipment with which a supply of oxygen or an air mixture for ventilating at least one person can be brought to this at least one person and ensured. It goes without saying that methods or mechanisms for ventilating more than one person may also be provided.

The autonomous aerial vehicle is also designed with communication methods or mechanisms for exchanging positional data and/or information. These are intended to comprise all technical possibilities for transmitting the position at the time of the autonomous aerial vehicle and/or information from or out of the autonomous aerial vehicle, for example, to a rescue control center, but also, for example, information from the rescue control center to or into the autonomous aerial vehicle. This makes possible a continuous analysis of the situation and an adaptation of all the required measures in the case concerned. With respect to the communication methods or mechanisms, transmitting may also be understood as transmission in the technical sense. Communication methods or mechanisms are therefore transmission methods or mechanisms, for example, transmitting and receiving devices for the transmission of information in the cellular network.

In the simplest case, and merely by way of example, the autonomous aerial vehicle may be designed as a drone which is equipped with a GPS system for positional determination and mobile access to the Internet or a cellular connection as communication methods or mechanisms. With this drone, ventilating methods or mechanisms can be brought to a location without being hindered by road-bound traffic or other restrictions. The disclosed aerial vehicle therefore makes it possible to quickly reach the person or persons that require ventilation irrespective of how well a location is served by transport links, whether the transport links are disturbed or destroyed, or how the traffic situation is at the time of the operation. According to the disclosure, it is also possible to launch a swarm, that is to say more than one autonomous aerial vehicle, to a location for the ventilation of multiple people, as still to be explained. The method or mechanism for recording the surrounding area on the one hand allow the procedures or actions followed by the drone to be adapted to the situation, on the other hand allow this information to be transmitted directly from the location concerned to the rescue control center and/or to rescue workers on the way to the location, so that they can prepare themselves for the specific situation at the scene.

In a first disclosed embodiment, methods or mechanisms for ventilating comprise at least one oxygen store and/or at least one oxygen mask. An oxygen store should be understood in this case as meaning a container in which an air mixture for ventilating persons, in particular, pure oxygen, is contained. Oxygen cylinders with capacities of two, five or ten liters are a suitable form, for example, since they can be exchanged quickly and easily as soon as they are depleted. An internal oxygen store may also be formed in the disclosed aerial vehicle and be filled with oxygen or an air mixture for ventilating one or more persons.

An oxygen mask is a device which covers the face, or at least the nose and the mouth, of a person to enable a person to breathe in oxygen or an air mixture for ventilation in a rescue situation, in particular, under aggravated external conditions.

Optionally, the at least one oxygen mask is connected to the at least one oxygen store. In this case, the oxygen mask may be connected directly to the oxygen store or be arranged on it; the oxygen mask may however also, for example, be connected to the oxygen store using a tube through which the oxygen or the air mixture for ventilating a person is delivered from the oxygen store to the oxygen mask. An exemplary aerial vehicle may also have multiple oxygen masks and/or multiple oxygen stores, it also being possible for multiple oxygen masks to be connected to one oxygen store.

Optionally, the at least one oxygen mask is of an extendable design. This is provided, on the one hand, to stow the at least one oxygen mask safely in or on the autonomous aerial vehicle during transport, and consequently to prevent damage or loss; on the other hand, in this way the at least one oxygen mask can be moved toward a person to be ventilated, so that the autonomous aerial vehicle can maintain a sufficient safety distance from the person to be ventilated. Moreover, an oxygen mask can also be extended to a person to be ventilated to whom the autonomous aerial vehicle cannot fly directly because of obstacles.

The oxygen mask is therefore moved from a transporting position into a ventilating position, in which the oxygen mask is moved substantially away from the aerial vehicle and toward the person to be ventilated, while it remains connected to the oxygen store.

The extending of the oxygen mask may be brought about, for example, by an oxygen tube, which is connected to the at least one oxygen store and is formed with mechanical links, which are pushed apart from one another in a longitudinal axis of the tube, in particular, are pushed apart from one another in a motorized manner. A suitable design with adjusting elements allows any desired form or any desired path of the tube to be set with respect to its longitudinal axis as it extends. Another disclosed embodiment given by way of example is the design with a tube that is held and guided by a robot arm to set an extended position.

In another disclosed embodiment, the autonomous aerial vehicle has methods or mechanisms for providing information and/or instructions on ventilating a person.

This should be understood as meaning all technical possibilities by which information and/or instructions on ventilating a person can be transmitted to an information recipient, such as, for example, a passerby, a first aider or a person to be ventilated if they are still conscious. Instructions on ventilation include instructions on what to do, how the oxygen mask is to be put on or how a person, for example, someone with an asthma attack, can be helped to breathe more easily.

The instructions may however also comprise measures intended to calm a first aider and/or the person to be ventilated, for example, by playing calming music or standardized questions given by voice control, for example, in relation to names, the weather and the like. First aiders should be understood as persons who are first to provide medical assistance, in particular, ventilating a person.

The information that can be provided by way of the suitable methods or mechanisms of the disclosed aerial vehicle is for example, information that rescue workers are on their way, how far away they are and when they will arrive, or whether there are dangers in the surrounding area, so that measures can be taken to remove those injured and first aiders from the danger zone or to eliminate the danger. Such information may be stored in a suitable way in the autonomous aerial vehicle, optionally be stored and/or retrieved in conjunction with a recording of the surrounding area. Alternatively or in addition, information may also be transmitted to the disclosed aerial vehicle from outside, for example, from a rescue control center.

The method or mechanism for providing information and/or instructions on ventilating a person may comprise at least one monitor, at least one display, at least one projector, at least one microphone and/or at least one loudspeaker.

A monitor and/or a display are suitable for transmitting graphic information, such as images or videos and/or text-based information and/or instructions. An exemplary aerial vehicle may be designed with monitors and/or displays such that in a flying position they can be safely retracted or folded in, so that they are not damaged during flight. At the location concerned, they can then be moved out of the flying position into a position for use, in which they can be seen by a first aider or a person to be ventilated.

Alternatively or in addition, at least one microphone may be provided, by which a first aider or a person to be ventilated can communicate by voice with the autonomous aerial vehicle and/or with a rescue control center and/or an emergency doctor connected to it. Answers and/or other auditive information can be transmitted by at least one loudspeaker. In this way, a first aider can also ask the rescue control center and/or the emergency doctor questions that arise while administering first aid.

The aerial vehicle may have at least one projector. With one or more projectors, graphic and/or text-based information can be projected and transmitted onto surfaces in the surrounding area of the location concerned. Furthermore, by one or more projectors, a zone around the person or persons to be ventilated that may only be entered by rescue workers, or exclusion zones, can be marked. Furthermore, if the person to be ventilated is conscious and can walk unassisted, one or more projectors may project waymarkers and/or directional indications onto a surface in the surrounding area of the person to be ventilated, to guide the person out of the danger zone and to safety. This may be assisted by lighting up the immediate vicinity by floodlights and the like.

In a next disclosed embodiment, the method or mechanism for positional determination inside and/or outside buildings comprise at least one GPS receiver, sensors for recording spatial information and/or methods or mechanisms for image-based determination of locational information. As already explained, these may be designed only for positional determination indoors, only for positional determination outside buildings or for both.

Sensors for recording spatial information may be, for example, air pressure sensors, which are designed to detect a change in the air pressure with increasing height, and, for example, thereby determine a floor within a building on which a person is to be found. Also on the basis of images or videos that are recorded by methods or mechanisms of a camera or other imaging processes, suitable methods can be used for detecting locations on the basis of characteristic objects and determining the position from them. This may include, for example, door signs in an office building that show names, company names and/or room numbers allowing conclusions to be drawn as to the position in the building.

A further method for positional determination indoors and also outside buildings is often referred to for simplicity as "ground GPS". In this case, a multiplicity of transmitters which transmit a GPS-synchronized time signal are distributed over a relatively large area, such as a town and/or company premises and/or within a building. By a suitable receiving device, these signals can be received and the position at the site of the receiving device can be determined by triangulation. Further methods by WLAN or BLUETOOTH® Low Energy are likewise possible for determining the position of the aerial vehicle according to the disclosure.

In another disclosed embodiment of the disclosed aerial vehicle, methods or mechanisms for recording the surrounding area comprise at least one camera, at least one sensor and/or methods or mechanisms for lighting up the surrounding area.

The at least one camera serves for graphically recording the surrounding area by images or videos. This allows the surrounding area to be graphically recorded and transmitted to a rescue control center, an emergency doctor and/or paramedic, so that the latter can get an overview of the rescue situation.

The sensors provided are designed for the purpose of recording or detecting, for example, temperatures, air pressure, atmospheric humidity and/or the presence of harmful substances. The recording of the surrounding area by radar or ultrasonic sensors is also covered by this disclosed embodiment. Obstacles, and consequently also walls, passages and the like, can be detected by radar or ultrasonic sensors. With heat sensors, thermal signatures of persons that require help and/or ventilation can be detected.

By the sensors in the autonomous aerial vehicle, emergency services can inform themselves before arrival at the location concerned, for example, in the surrounding area of a fire, whether the fire has caused harmful substances to be released, and as a consequence on the one hand whether they should themselves put on a breathing mask and on the other hand whether they should take corresponding precautions for treating the person or persons at the location.

Methods or mechanisms for lighting up the surrounding area are of great benefit, since they allow the surrounding area to be seen in the first place in a meaningful way, whether by an emergency doctor and/or paramedic or by a camera. Optionally, a mechanism for lighting may be floodlights. With at least one floodlight, the surrounding area of the disclosed aerial vehicle can be lit up, whereby it is made possible in the first place to find persons to be ventilated in dark spaces or when there is no daylight or to record the surrounding area by cameras or the like. At the same time, the lighting allows rescue workers on arrival to find the autonomous aerial vehicle, and consequently persons to be ventilated, more quickly. Optionally, an exemplary aerial vehicle has a multiplicity of floodlights, which are ideally aligned in different directions, in this way to be able to light up the surrounding area of the autonomous aerial vehicle specifically and selectively.

In yet a further disclosed embodiment, the aerial vehicle can be called up by the emergency call function of a mobile terminal and/or a transportation vehicle, in particular, with the transmission of locational information applicable at the time.

Mobile terminals such as tablets or cell phones, but also transportation vehicles, today often have an emergency call function. With this emergency call function, in an emergency situation a user can initiate an emergency call, for example, a phone call. This may take place by active initiation by the user, by a corresponding operating element on the mobile terminal or in the transportation vehicle, or automatically, if the mobile terminal or the transportation vehicle detects an emergency situation. The detection of emergency calls usually takes place on the basis of sensor data, which, for example, allow an accident to be inferred. Instead of a phone call being made by voice for the transmission of an emergency, the information recorded by the mobile terminal or the transportation vehicle by sensors may also be transmitted as an emergency call. Optionally, in all disclosed embodiments, the position of the mobile terminal and/or the transportation vehicle at the time, and consequently the location of the emergency, is transmitted.

When the emergency call is initiated, it may be transmitted directly to a rescue control center, which then initiates the launch of one or more aerial vehicles, which provide methods or mechanisms for ventilating one or more persons.

In an alternative, the emergency call is not transmitted to the rescue control center, or not only to the rescue control center, but directly to a nearby disclosed aerial vehicle. Thus, the time between the initiation of the emergency call and the launch of the aerial vehicle is minimized. This may be realized, for example, by an app on a mobile terminal or in a vehicle in which the positions of available autonomous aerial vehicles are stored. Moreover, direct communication with the autonomous aerial vehicles is possible by the app. If an emergency occurs, the app determines the closest location of an exemplary aerial vehicle, transmits the emergency call to it and launches the aerial vehicle to the location concerned. At the same time or after that, the necessary information is transmitted to a rescue control center, which sends an emergency doctor and/or paramedic to the location.

It goes without saying that an emergency may also be detected by smoke alarms or other methods or mechanisms for monitoring a building and be transmitted to a rescue control center and/or the disclosed aerial vehicle. In this case, the procedures already stated also apply to this disclosed embodiment for initiating an emergency call.

Likewise claimed is a method for ventilating at least one person with an exemplary autonomous aerial vehicle invention, comprising at least the following:
transmitting a need for ventilation to the aerial vehicle,
transmitting the target position of the need for ventilation to the aerial vehicle,
flying to the target position of the need for ventilation,
recording the surrounding area and at least one person to be ventilated at the target position of the need for ventilation,
sensing a face of the at least one person to be ventilated, and
placing the oxygen mask on the face of the at least one person to be ventilated.

The need for ventilation is in this case the information that one or more persons must be ventilated. As already stated, this information is transmitted by way of an emergency call to a rescue control center and/or directly to an exemplary aerial vehicle. In this case, the approximate or, if possible, exact position of the person or persons to be ventilated is also transmitted. This position is the target position of the autonomous aerial vehicle. The aerial vehicle is launched immediately and flies to the target position. During the flight, further information and/or amended information may be transmitted to the autonomous aerial vehicle.

Having arrived at the target position, the autonomous aerial vehicle determines with the method or mechanism for recording the surrounding area the immediately surrounding area and, if required, the exact position of one or more persons to be ventilated. Once the person to be ventilated or the persons to be ventilated at the target position have been recorded, the face of a person to be ventilated is sensed and the oxygen mask is placed on the face, particularly by extending the oxygen mask, as already explained. If the aerial vehicle is equipped with multiple oxygen masks, and if there is a second person to be ventilated in the immediate vicinity, and consequently within the range of the second oxygen mask, the face of this person can also be detected and the oxygen mask placed on it.

If, when recording the surrounding area, further persons with a need for ventilation were detected, this may be transmitted to the rescue control center by the communication method or mechanism, so that further disclosed aerial vehicles can be sent to the target position.

Disclosed aerial vehicles may be stationed on roofs of houses or other elevated points in urban areas or in the country. It is also within the scope of the disclosure for them to be stationed inside buildings. At the locations where they are stationed, the energy stores of the aerial vehicles are charged; they can be maintained and/or newly filled with oxygen or air mixture for ventilating persons. To protect them from the effects of the weather and/or from being damaged, they may be provided in boxes or compartments, which may be of a closable design. As an alternative to this, once its mission has been completed or when the energy store and/or the oxygen stores are depleted, an exemplary aerial vehicle may fly to a maintenance station in the vicinity, and return to its original location after completion of the maintenance and/or the filling of the oxygen store or stores.

The disclosed autonomous aerial vehicle can be used in a wide variety of operations. Some examples are fires in buildings, ventilating a person saved from drowning, medical emergencies after accidents or fires in aircraft that have made emergency landings.

Unless otherwise stated in an individual case, the various embodiments of the disclosure mentioned in this application can be combined with one another.

FIG. 1 shows an exemplary aerial vehicle 10, which is designed with four rotors 12. The autonomous aerial vehicle 10 also has methods or mechanisms for positional determination inside and outside buildings (not shown), so that use is possible in both areas and also in combinations of the areas. For use outside buildings, a GPS receiver is provided for this; indoors, the locational determination is intended to be brought about by image-based methods.

The autonomous aerial vehicle 10 is likewise equipped with communication methods or mechanisms for exchanging positional data and/or information (not shown), so that, for example, the position of the aerial vehicle 10 can be transmitted to a rescue control center by way of the cellular network and the rescue control center can transmit a target position or further information about the incident to the autonomous aerial vehicle 10.

The main body of the aerial vehicle 10 is of an approximately cuboidal configuration and has at each of its rounded corners a floodlight 16 for lighting up the surrounding area. The four floodlights 16 can be switched on and off independently of one another, to light up the surrounding area specifically and selectively. For recording the surrounding area, cameras 14 and sensors 20 are provided. Some of the sensors 20 on the aerial vehicle 10 are designed to record the surrounding area by radar.

Consequently, the aerial vehicle 10 with the cameras 14 and sensors 20 can record the surrounding area, that is to say whether, for example, there are obstacles in its flight path, but also one or more persons to be ventilated can thus be recorded by the aerial vehicle 10. The images and/or videos that are created with the cameras 14 can be analyzed by an internal evaluation unit, or they are transmitted to the rescue control center and evaluated there.

One of the cameras 14 is designed to record thermal images. Thermal images are used to visualize infrared radiation, and thereby infer the presence of heat sources, such as, for example, persons, on the basis of differences in temperature in an image or video.

By the sensors 20, moreover, harmful substances can be detected and height information obtained, for example, allowing conclusions to be drawn as to a floor within a building on which a person is being ventilated.

The aerial vehicle is designed with methods or mechanisms for facial detection (not shown). The images recorded by cameras 14 are consequently analyzed for the presence of persons and furthermore for the position of the faces of the persons. On the basis of the evaluation by facial detection, the autonomous aerial vehicle 10 can place an oxygen mask 34 onto a face, or at least onto the mouth and nose of a person to be ventilated.

In this disclosed embodiment given by way of example, for this the autonomous aerial vehicle 10 extends an oxygen store 30, a tube 32 and the oxygen mask 34 out of the transporting position into a ventilating position, as shown in FIG. 1. The oxygen store 30 is filled with oxygen or an air mixture for ventilating persons. The oxygen mask 34 and the oxygen store 30 are connected to one another by the tube 32. Through the tube 32, oxygen or an air mixture for ventilating a person can be delivered from the oxygen store 30 to the oxygen mask 34. The tube 32 is in this case designed such that its length and its path along its longitudinal axis can be set such that the ventilation of the person can be ensured without endangering the person by the aerial vehicle 10 coming too close to the person.

The oxygen mask 34 is designed with two sensors 36. By these sensors, the contact of the oxygen mask 34 with the person to be ventilated, that is to say the correct placement, can be detected.

Furthermore, the aerial vehicle 10 is designed with a projector 18. If the person to be ventilated is conscious, information can thereby be projected onto the ground next to the person to transmit information to the person. This may be the imminent arrival of the rescue workers, or else a request to get out of the danger zone and directions on how to achieve this.

Two incidents are to be outlined below, but should only be understood as examples.

In the first case, a fire has spread on the eighth floor of a tall building. It was possible for some people to be evacuated in time, while others have already lost consciousness. The stifling and smoke-filled air spreads throughout the floor. An emergency call has been initiated by the smoke detectors in the building, and one person was able to use their phone to initiate an emergency call by the emergency call function. The fire service is on their way to the location concerned. The autonomous aerial vehicles 10 stationed in the building have also been activated by the emergency call. The information that the eighth floor is on fire and that there are persons still there has already been transmitted with the emergency call. At least an approximately exact positional indication of a person to be ventilated is known as a result of the emergency call that was initiated by the emergency call function on the phone.

The aerial vehicles 10 fly to the eighth floor, using their methods or mechanisms for positional determination to orient themselves in the building. Having arrived at the eighth floor, the surrounding area is recorded by cameras 14 and sensors 20 and evaluated, to make it possible for them to advance and find the persons to be ventilated. To facilitate this, the floodlights 16 are also switched on.

If a person is sensed by one of the aerial vehicles 10, the face of the person is detected and the oxygen mask 34 is placed on the face of the person, or at least on the mouth and nose of the person. For this purpose, the oxygen mask 34 with the tube 32 and the oxygen store 30 is extended from the transporting position into the ventilating position and thereby moved toward the person. Ventilation is maintained until the rescue workers are on the scene. The sensors 36 in this case record whether the oxygen mask 34 is placed on the face of the person to be ventilated. All further aerial vehicles 10 behave in the same way.

During the ventilation, the aerial vehicle 10 transmits its exact position to the rescue control center and/or the rescue workers. On the basis of the transmitted position of the aerial vehicle 10 and the lighting by the floodlights 16, the rescue workers can on arrival quickly find the aerial vehicle 10, and consequently also the person to be ventilated. Once this has happened, the aerial vehicle 10 flies to a nearby maintenance station, is checked there and, if appropriate, repaired and the oxygen store 30 exchanged for a filled oxygen store 30. Subsequently, the aerial vehicle 10 flies back to its original location until the next mission.

In a second case, a pilot notices on the approach to landing that the landing gear cannot be deployed and notifies the control tower at the airport to alert the rescue services. During the landing of the aircraft, a fire breaks out. Some of the passengers can be evacuated after landing, others become unconscious because of the development of smoke in the aircraft. The emergency call made by the pilot also activated autonomous aerial vehicles 10 stationed within the precincts of the airport and they fly to the aircraft. In this case, they are much quicker than the other rescue workers.

Having arrived at the aircraft, the aerial vehicles 10 can, as described in the previous case, find the persons still located within the aircraft and ventilate them until the rescue workers arrive.

LIST OF REFERENCE SIGNS

10 Autonomous aerial vehicle
12 Rotor
12 Camera
16 Lighting, floodlight
18 Projector 20 Sensor
30 Oxygen store
32 Tube
34 Oxygen mask
36 Sensor

The invention claimed is:

1. An autonomous aerial vehicle for ventilating a person, the autonomous aerial vehicle comprising:
    means for positional determination inside and/or outside buildings;
    means for recording the surrounding area;
    means for ventilating the person;
    communication means for exchanging positional data and/or information; and
    means for facial detection, wherein the means for facial detection is configured to determine the mouth and/or nose of the person to be ventilated for correctly fitting a mask of the means for ventilating the person.

2. The aerial vehicle of claim 1, wherein the means for ventilating comprise at least one oxygen store and/or at least one oxygen mask.

3. The aerial vehicle of claim 2, wherein the at least one oxygen mask is extendable.

4. The aerial vehicle of claim 1, further comprising means for providing information and/or instructions for ventilation.

5. The aerial vehicle of claim 4, wherein the means for providing information and/or instructions for ventilating comprise at least one monitor, at least one display, at least one projector, at least one microphone and/or at least one loudspeaker.

6. The aerial vehicle of claim 1, wherein the means for positional determination inside and/or outside buildings comprise at least one GPS receiver, sensors for recording spatial information and/or means for image-based determination of locational information.

7. The aerial vehicle of claim 1, wherein the means for recording the surrounding area comprise at least one camera, at least one sensor and/or means for lighting up the surrounding area.

8. The aerial vehicle of claim 1, wherein the aerial vehicle is called up using the emergency call function of a mobile terminal and/or a transportation vehicle with the transmission of locational information applicable at the time.

9. A method for ventilating at least one person with an autonomous aerial vehicle, the method comprising:
    transmitting a need for ventilation and a target position to the aerial vehicle;
    controlling flight of the aerial vehicle to the target position of the need for ventilation;
    recording the surrounding area and at least one person to be ventilated at the target position of the need for ventilation;
    sensing a mouth and/or nose of the at least one person to be ventilated for correctly fitting a mask of the means for ventilating the at least one person, with the aerial vehicle; and
    placing the oxygen mask on the face of the at least one person to be ventilated.

10. The method of claim 9, further comprising flowing at least some oxygen from at least one oxygen store via oxygen mask to ventilate the at least one person.

11. The method of claim 9, further comprising presenting user instructions for ventilation on at least one display of the aerial vehicle.

12. The method of claim 9, wherein the need for ventilation is transmitted as emergency call function of a mobile terminal and/or a transportation vehicle near the target position.

* * * * *